US00PP09192P

United States Patent [19]

Alston

[11] Patent Number: Plant 9,192

[45] Date of Patent: Jul. 11, 1995

[54] PEAR TREE—CONCORDE VARIETY

[75] Inventor: Frank H. Alston, Maidstone, United Kingdom

[73] Assignee: Plant Breeding International Cambridge Limited, Cambridge, United Kingdom

[21] Appl. No.: 179,352

[22] Filed: Jan. 10, 1994

[51] Int. Cl.[6] ..... A01H 5/00

[52] U.S. Cl. ..... Plt./36

[58] Field of Search ..... Plt. 36

*Primary Examiner*—James R. Feyrer

*Attorney, Agent, or Firm*—Burns, Doane, Swecker & Mathis

[57] ABSTRACT

A new and distinct variety of high yielding dessert pear is provided which originated as a cross between the Doyenné Du Comice variety (non-patented in the United States) and the Conference variety (non-patented in the United States). The fruit is elongated and assumes an attractive yellow skin coloration with a slight pink overcolor at those areas exposed to the sun. Trees of the new variety normally come into bearing earlier than those of the Conference variety under growing conditions encountered in the United Kingdom. The russet of the fruit is slight when compared to that of the Conference variety and tends to be distributed over the whole fruit. The fruit of the new variety unlike that of the Conference variety retains a slight crispness when fully ripe and possesses a flavor that is fuller and more aromatic. The picking season for the fruit is later than for the Conference variety. The leaves exhibit an impressive dark green coloration. Unlike the Conference variety, the new variety appears to be tolerant to Parry's Syndrome/Pear Decline.

2 Drawing Sheets

SUMMARY OF THE INVENTION

The new variety of pear tree (i.e., *Pyrus communis* L.) was created by artificial pollination wherein two parents were crossed which previously had been studied in the hope that they would contribute the desired characteristics. The female parent (i.e., seed parent) was the Doyenné Du Comice variety (non-patented in the United States), and the male parent (i.e., pollen parent) was the Conference variety (non-patented in the United States). The parentage of the new variety can be summarized as follows:

Doyenné Du Comice × Conference.

Such pollination was carried out during 1968 at the East Malling Research Station, East Malling, Maidstone, Kent, England. The seeds resulting from this pollination were sown and plants were obtained that were physically and biologically different from each other. Selective study resulted in the identification of a single plant of the new variety. The new variety of the present invention initially was designated P22B/14, and first fruited and was selected during 1977.

It was found that the new pear variety of the present invention possesses the following combination of characteristics:

(a) forms attractive dark green leaves,
(b) is precocious and fruits at an earlier age than the Conference variety,
(c) forms attractive yellow fruit following storage with a slight pink overcolor where exposed to the sun generally with only a slight russet over the whole fruit unlike the Conference variety,
(d) forms fruit that when fully ripe exhibits a flesh that retains a slight crispness unlike the Conference variety, (e) forms fruit that exhibits a fuller and more aromatic flavor than the Conference variety, and
(f) exhibits a picking season that is later than the Conference variety.

It has been found that the new variety is capable of being pollinated by the Conference, Comice, and Williams varieties, and also is capable of pollinating these same varieties.

The fruit size of the new variety tends to be similar to that of the Conference variety with a higher percentage of fruits commonly having a maximum diameter greater than 55 mm and 60 mm. The new variety commonly forms a lesser quantity of misshapen fruit than the Conference variety. Also, the cumulative fruit yields for a given number of trees planted at a specified density has been found to be substantially greater for the new variety than for the Conference and Comice varieties. Accordingly, the cumulative yields, fruit sizes, and the cropping efficiency for the new variety tend to be greater than those of the Conference variety with no diminution in the percentage of fruits that grade Class 1.

The extreme precocity of the new variety from time of planting to fruiting can possibly lead to over-cropping from an early age with concomitant branch breakage and biennial bearing. Accordingly, it may be desirable to thin the fruit during at least the early years, and to take steps to modify and strengthen branch angles so as to improve the ability to carry a large fruit load without substantial breakage. For instance, the branch angles without modification tend to be upright and to become pendulous when under cropping. Without training such branch angles may tend to be narrow which can lead to weakness. Once strengthened through angle modification it has been found that the branches of the new variety are better able to carry a large pear crop load without any substantial breakage.

The optimum picking date for the new variety when intended for CA storage was approximately Oct. 10th during 1991-1992, though fruit picked on earlier dates also was found to be acceptable for storage. In comparison, the overall optimum picking date for the Conference variety was approximately Sep. 17th during 1991-1992. The fruit of the new variety can be stored at a low concentration of oxygen until April with a good retention of aroma and flavor.

The flesh of the new variety when ripe retains a slight crispness while that of the Conference variety is more melting.

Preferred rootstocks for use with the new variety are Quince East Malling A and Quince East Malling C. No latent graft incompatibility has been observed with Quince A or Quince C. To date, the new variety has always cropped more heavily on Quince East Malling C. However, there is some indication that the individual fruits are slightly larger (e.g., 91 to 95 percent have a maximum diameter greater than 60 mm vs. 84 to 86 percent), and perhaps a higher percentage meet the Class 1 standard (e.g., 89 to 90 percent vs. 83 to 90 percent) when produced on Quince East Malling A rootstock instead of Quince East Malling C rootstock. Quince East Malling A rootstock may be preferred when the new variety is grown on heavier soils.

The new variety is believed to be susceptible to fireblight to approximately the same degree as the Doyenné Du Comice variety.

To date, the new variety appears to be tolerant to Parry's Syndrom/Pear Decline unlike the Conference variety that exhibits sensitivity. Also, the dark green coloration of the leaves of the new variety (as illustrated) is impressive.

The performance of the new variety has been evaluated at East Malling Research Station, and at the National Fruit Trials at Brogdale, Kent ME13 8XZ England during 1983.

The new variety has been asexually reproduced by budding and grafting in England using EMLA status foundation stock. The characteristics of the new variety have been found to be stable and to be capable of transmission through succeeding generations of such propagation.

The new variety has been named the Concorde variety.

BRIEF DESCRIPTION OF THE PHOTOGRAPHS

The accompanying photographs show typical specimens of the new variety as depicted in color as nearly true as it is reasonably possible to make the same in color illustrations of this character. FIGS. 1 and 2 were prepared during the 1983 National Fruit Trials.

Figure 3:
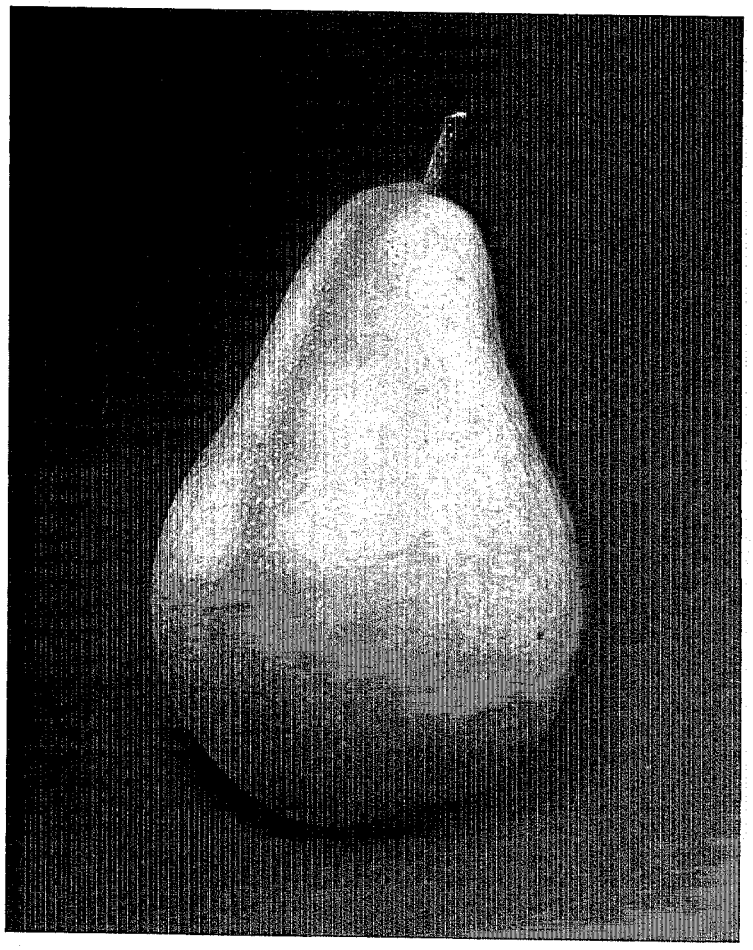

FIG. 3 illustrates a typical mature fruit of the Concorde variety. The storage has been conducted approximately two weeks after picking in air at 4° C. A pink overcolor is visible on the left side of the fruit that previously was exposed to the sun. The overall skin surface is shown to be smooth, and a light russet is visible. The lenticels additionally are apparent and are inconspicuous at the top right unrusseted area and are more conspicuous at the pink/russeted area at the left. The heavy russeting sometimes exhibited by the Conference variety is absent.

DETAILED DESCRIPTION

The following is a detailed description of the new Concorde pear variety. Color references are made while referring to the R.H.S. Colour Chart of the Royal Horticultural Society, London, England. The specimens described were grown primarily during the 1983 National Fruit Trials in England while present on Quince East Malling A rootstock.

Tree:

*Habit of branches.*—Spreading; however, branches tend to be upright but become pendulous under cropping, and without training the branch angles may be narrow and somewhat weak.

*Size of bulge at the graft.*—Large.

*One year old tree.*—Medium vigor, medium growth, straight with none or very few side shoots.

*One year old shoot.*—The length of the internodes is short, the color on the sunny side is brown, many lenticels are present, the size of the vegetative bud is medium, and the position of the vegetative buds relative to the shoots is medium free.

*Bark.*—The mature bark on one year-old shoots commonly is somewhat furrowed, the lenticels are conspicuous, and coloration approaches Grey-Brown Group 199A. In contrast the comparable bark of the Conference variety is smooth, the lenticels are inconspicuous, and the coloration is Greyed-Orange Group 165B, and that of the Comice variety is somewhat furrowed, the lenticels are more conspicuous and the coloration is Greyed-Orange Group 165A and 166A. When the mature tree trunks are compared both the Concorde and Conference varieties have smooth orange-brown bark commonly with some grey flakes on the south side of the tree and commonly more grey and flaking on the north side of the tree. In contrast the Comice variety has more conspicuous lines of horizontal lenticels.

Leaves:

*Leaf configuration.*—Generally uncupped, generally horizontal attitude, obtuse — angled at base, right-angled at the upper part, cuspidate at the tip, crenate margin with shallow indentations, medium length of the blade, the blade length:-breadth ratio is high, the curvature of the midrib is strong, the angle of the petiole with shoot is approximately 30° to 60°, the length of the petiole is long (e.g., approximately 30.1 mm. on average), and a stipule commonly is present.

*Leaf dimensions.*—Approximately 78.2 mm. in length an average, and approximately 40.9 mm. in width on average when measured during 1982/1983.

Figure 1:
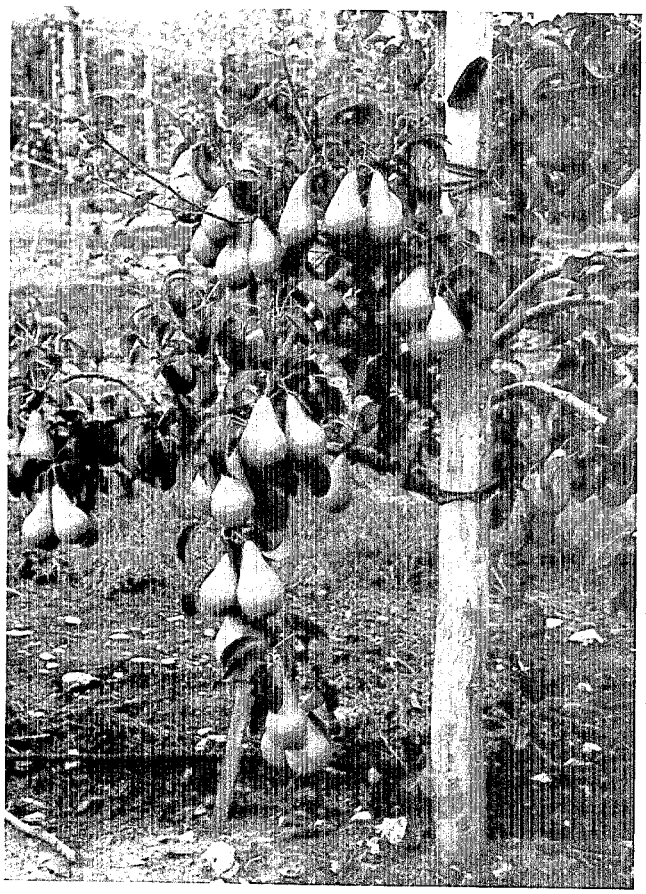
FIG. 1 illustrates a four or five year tree bearing a heavy crop of immature fruit. This shows the ability of the Concorde variety to abundantly bear large fruit at an early age unlike the Conference variety.
Figure 2:
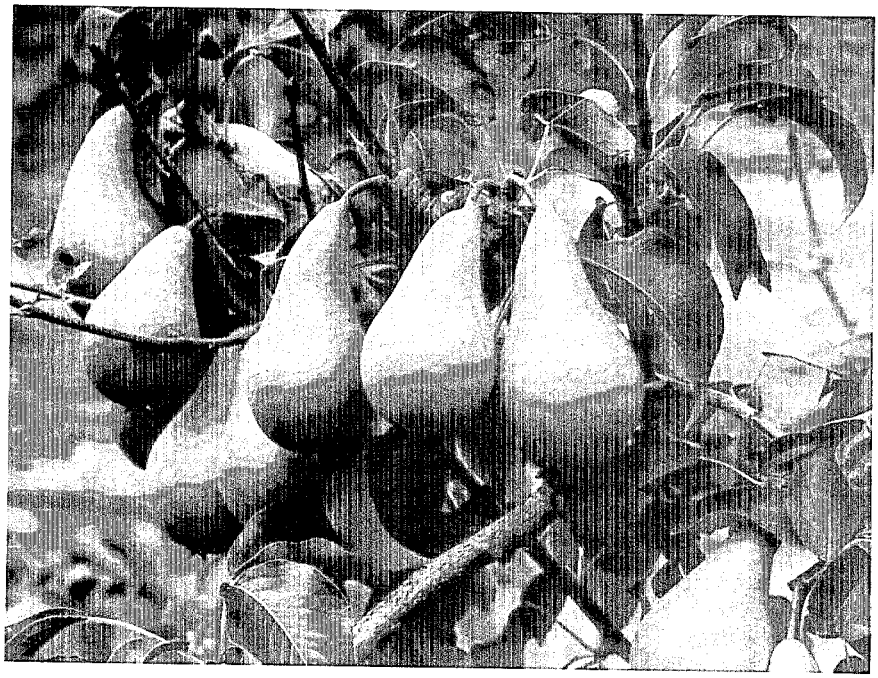
FIG. 2 illustrates a closer view of typical immature fruit present on the tree of FIG. 1.

*Leaf color.*—Dark green semi-glossy upper surface and lighter green under surface (as illustrated). As seen in FIG. 2, the upper surfaces of mature leaves commonly approach Yellow-Green Group 147A, and the under surfaces commonly approach Yellow-Green Group 147B in coloration. When fall coloration was observed on Oct. 11, 1994, the upper surface coloration at leaf midpoints varied and included Yellow-Green Group 146A, Yellow-Green Group 147A, and Greyed-Purple Group 187A; the under surface at leaf midpoints was primarily Yellow-Green Group 148B, and Yellow-Green Group 147C; the upper surface leaf tips varied greatly and included Greyed-Purple Group 187C, and Yellow-Green Group 147C; and the lower surface of the leaf tips was primarily Yellow-Green Group 147C, 148B, 148C, and 153D.

*Young shoot.*—Reddish-green in coloration at the extremity with strong pubescence at the tip.

*Terminal growth.*—When measured on Oct. 11, 1994 on trees planted during the Spring of 1988 on Quince East Malling C rootstock at spacings of 1.75 m.×3.5 m., the new terminal growth was approximately 11.4 cm.

Inflorescence:

*Season of flowering.*—Later than the Comice variety, with full flower on May 9, 1993.

*Bud shape.*—Elongated and pointed, mainly on spurs.

*Number of flowers.*—Medium, approximately 6 to 7 on average, commonly with terminal clusters of 9, each with overlapping petals.

*Time of flowering.*—80 percent on May 9, 1983.

*Pedicels.*—Long, longer than that of the Williams variety, with medium pubescence.

*Sepals.*—Long in length and generally horizontal.

*Petals.*—Approximately 16 to 19 mm in length including the claw which can be compared to approximately 12 to 15 mm for the Williams variety, greater in length than in width, U-shaped at base, strong undulation of margins, with medium claw length. The petal color for the Concorde variety is white and is typical of Pyrus in general.

*Stigmas.*—Of approximately the same height as the anthers.

*Anthers.*—Medium in size.

*Pollen.*—Cream/yellow in coloration and typical of Pyrus.

*Receptacle.*—Slightly hollowed.

*Fruit.*—Elongated with maximum diameter towards the base, medium in size, generally symmetrical in longitudinal section, concave in profile, the ground color of the skin is yellow and the overcolor is pink (as illustrated) and tends to appear at areas exposed to the sun, a slight amount of russet tends to be distributed over the whole fruit, the length and thickness of the slightly curved stalk are medium, the insertion of the stalk is oblique, the stalk cavity is absent or very shallow, the size of the eye is large and even exceeds in size that of the Conference variety, the eye is open, the long sepals are spreading, the depth of the eye basin is shallow, the breadth of the eye basin is narrow, the margin of the eye basin is slightly ribbed, the diameter of the core is medium, the shape of the cells of the core is elongated, the seeds are elongated, the texture of the fruit is medium, the juiciness of the flesh is medium, and the taste of the fruit is full, sweet, and aromatic.

The season of maturity for picking is medium. The ploidy level is diploid.

The taste of the fruit is pleasant, sweet and similar to that of the Conference variety, but commonly exhibits more aroma. The fruit texture generally is free from stone cells.

The fruit shape of the Concorde variety is similar to that of the Conference variety, but tends to be more lopsided. The seed locules and core characteristics of the Concorde variety are more similar to those of the Conference variety than those of the Comice variety. The seeds of the Comice variety tend to be larger than those of the Concorde and Conference varieties. Like the Comice variety the stone cells tend to be more prominent in the lower part of the cores of the Concorde variety than in the Conference variety.

On Oct. 17, 1994, thirty fruits each of the Concorde, Comice, and Conference varieties were obtained from air storage and were examined. Inconspicuous lenticels were visible on all parts of the Concorde fruit with a smooth surface, and russet was present on all fruits and covered greater than 50 percent of surface area on approximately $\frac{1}{3}$ of the fruits examined. On the fruit of the Concorde variety the lenticels generally became more conspicuous when they were russeted; however, where the russet coalesced to form patches, the lenticels were not as readily apparent. The fruit of the Comice variety possessed larger lenticels than the Concorde variety. In contrast all fruit of the Conference variety exhibited a smooth to rough russet over approximately 75 percent or more of the surface, and it was very difficult to see the lenticels.

When the fruit coloration of the Concorde variety was evaluated on Oct. 7, 1994, the ground color was found to vary from approximately Yellow-Green Group 151A to 152B. Fruit surfaces exposed to the sun have an overcolor that appears as fairly indistinct stripes on up to approximately $\frac{1}{3}$ of the surface and commonly is Greyed-Orange Group 171A and 171B. A similar overcolor is seen on the Comice variety, but not on the Conference variety. Experience indicates that following storage of the fruit of the Concorde variety the ground color commonly develops to that of Yellow Group 10 or 11 as seen in FIG. 3. The russet can coalesce on some fruits to cover 50 percent or more of the fruit surface, and the distribution of the russet varies.

I claim:

1. A new and distinct variety of pear tree having the following combination of characteristics:

(a) forms attractive dark green leaves, (b) is precocious and fruits at an earlier age than the Conference variety, (c) forms attractive yellow fruit following storage with a slight pink overcolor where exposed to the sun generally with only a slight russet over the whole fruit unlike the Conference variety, (d) forms fruit that when fully ripe exhibits a flesh that retains a slight crispness unlike the Conference variety, (e) forms fruit that exhibits a fuller and more aromatic flavor than the Conference variety, and (f) exhibits a picking season that is later than the Conference variety;

substantially as herein shown and described.

* * * * *